United States Patent [19]

Zanno et al.

[11] Patent Number: 4,603,012

[45] Date of Patent: Jul. 29, 1986

[54] L-AMINODICARBOXYLIC ACID ALKANES

[75] Inventors: Paul R. Zanno, Nanuet; Ronald E. Barnett, Suffern; Glenn M. Roy, Garnerville, all of N.Y.

[73] Assignee: General Foods Corporation, White Plains, N.Y.

[21] Appl. No.: 730,975

[22] Filed: May 6, 1985

[51] Int. Cl.$^4$ ............................................. C07K 5/06
[52] U.S. Cl. ............................................. 530/998.21
[58] Field of Search ............................... 260/112.5 R

[56] References Cited

U.S. PATENT DOCUMENTS 3,695,898 10/1972 Hill et al. ................... 260/112.5 R

FOREIGN PATENT DOCUMENTS 1325368 8/1973 United Kingdom .

OTHER PUBLICATIONS

Ariyoshi et al., *Bulletin of the Chemical Society of Japan*, 47(2), 326–330 (1974).
Tsang et al., *J. Med. Chem.*, 27, 1663–1668 (1984).

*Primary Examiner*—Delbert R. Phillips
*Assistant Examiner*—F. T. Moezie
*Attorney, Agent, or Firm*—Linn I. Grim; Thomas A. Marcoux; Daniel J. Donovan

[57] ABSTRACT

This invention relates to novel sweeteners of the formula:

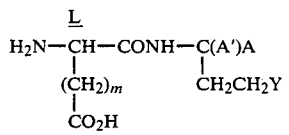

wherein
A is hydrogen, alkyl containing 1–3 carbon atoms, hydroxyalkyl containing 1–3 carbon atoms, alkoxymethyl wherein the alkoxy contains 1–3 carbon atoms or —$CO_2R$ in which R is alkyl containing 1–3 carbon atoms;
A' is hydrogen or alkyl containing 1–3 carbon atoms;
A and A' taken together with the carbon atom to which they are attached form cycloalkyl containing 3–4 carbon atoms;
Y is —$(CHR_2)_n$—$R_1$ or —$CHR_3R_4$;
$R_1$ is alkyl-substituted cycloalkyl, cycloalkenyl, bicycloalkyl or bicycloalkenyl containing at least one alkyl in the β-position of the ring, up to 7 ring carbon atoms and up to a total of 12 carbon atoms;
$R_2$ is H or alkyl containing 1–4 carbon atoms;
$R_3$ and $R_4$ are each cycloalkyl containing 3–4 ring carbon atoms;
n=0 or 1; and
m=0 or 1;

and food-acceptable salts thereof.

17 Claims, No Drawings

L-AMINODICARBOXYLIC ACID ALKANES

FIELD OF THE INVENTION

This invention relates to a novel group of compounds and more particularly to a novel group of compounds particularly well suited as sweeteners in edible foodstuff.

DESCRIPTION OF THE PRIOR ART

Sweetness is one of the primary taste cravings of both animals and humans. Thus, the utilization of sweetening agents in foods in order to satisfy this sensory desire is well established.

Naturally occuring carbohydrate sweeteners such as sucrose, are still the most widely used sweetening agents. While these naturally occurring carbohydrates, i.e., sugars, generally fulfill the requirements of sweet taste, the abundant usage thereof does not occur without deleterious consequence, e.g., high caloric intake and nutritional imbalance. In fact, oftentimes the level of these sweeteners required in foodstuffs is far greater than the level of the sweetener that is desired for economic, dietetic or other functional consideration.

In an attempt to eliminate the disadvantages concomitant with natural sweeteners, considerable research and expense have been devoted to the production of artificial sweeteners, such as for example, saccharin, cyclamate, dihydrochalcone, aspartame, etc. While some of these artificial sweeteners satisfy the requirements of sweet taste without caloric input, and have met with considerable commercial success, they are not, however, without their own inherent disadvantages. For example, many of these artificial sweeteners have the disadvantages of high cost, as well as delay in the perception of the sweet taste, persistent lingering of the sweet taste, and very objectionable bitter, metallic aftertaste when used in food products.

Since it is believed that many disadvantages of artificial sweeteners, particularly aftertaste, is a function of the concentration of the sweetener, it has been previously suggested that these effects could be reduced or eliminated by combining artificial sweeteners such as saccharin, with other ingredients such as aspartame or natural sugars, such as sorbitol, dextrose, maltose, etc. These combined products, however, have not been entirely satisfactory either. Some U.S. Patents which disclose sweetener mixtures include for example, U.S. Pat. No. 4,228,198; U.S. Pat. No. 4,158,068; U.S. Pat. No. 4,154,862; and U.S. Pat. No. 3,717,477.

Accordingly, much work has continued in an attempt to develop and identify compounds that have a sweet taste and which will satisfy the need for better lower calorie sweeteners. Search continues for sweeteners that have intense sweetness, that is, deliver a sweet taste at low use levels and which will also produce enough sweetness at low levels to act as sole sweetener for most sweetener applications. Furthermore, the sweeteners sought must have good temporal and sensory qualities. Sweeteners with good temporal qualities produce a time-intensity sweetness response similar to natural sweeteners without lingering. Sweeteners with good sensory qualities lack undesirable off tastes and aftertaste. Furthermore, these compounds must be economical and safe to use.

In U.S. Pat. No. 3,798,204, L-aspartyl-O-t-butyl-L-serine methyl ester and L-aspartyl-O-t-amyl-L-serine methyl ester are described as sweet compounds having significant sweetness.

In U.S. Pat. No. 4,448,716 metal complex salts of dipeptide sweeteners are disclosed. In the background of this patent a generic formula is described as an attempt to represent dipeptide sweeteners disclosed in four prior patents: U.S. Pat. No. 3,475,403; U.S. Pat. No. 3,492,131; Republic of South Africa Pat. No. 695,083 published July 10, 1969; Republic of South Africa Pat. No. 695,910 published Aug. 14, 1969. The general formula attempting to represent these patents is as follows:

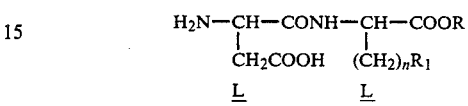

wherein R represents the lower alkyls, lower alkylaryls and cycloalkyls, n stands for integers 0 through 5, $R_1$ represents (a) phenyl group, (b) lower alkyls, (c) cycloalkyls, (d) $R_2$.

Where $R_2$ is hydroxy, lower alkoxy, lower alkyl, halogen, (e) $S(O)_m$ (lower alkyl) where m is 0, 1 or 2 and provided n is 1 or 2, (f) $R_3$.

Where $R_3$ represents an hydroxy or alkoxy and (g) single or double unsaturated cycloalkyls with up to eight carbons. These compounds also are not entirely satisfactory in producing a high quality sweetness or in producing a sweet response at lower levels of sweetener.

Dipeptides of aspartyl-cysteine and aspartylmethionine methyl esters are disclosed by Brussel, Peer and Van der Heijden in *Chemical Sense and Flavour*, 4, 141–152 (1979) and in *Z. Lebensm. Untersuch-Forsch.*, 159, 337–343 (1975). The authors disclose the following dipeptides:

α-L-Asp-L-Cys(Me)-OMe
α-L-Asp-L-Cys(Et)-OMe
α-L-Asp-L-Cys(Pr)-OMe
α-L-Asp-L-Cys(i-Pr)-OMe
α-L-Asp-L-Cys(t-But)-OMe
α-L-Asp-L-Met-OMe

In U.S. Pat. No. 4,399,163 to Brennan et al., sweeteners having the following formulas are disclosed:

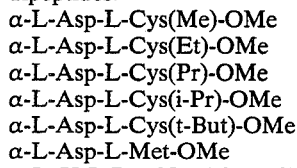

and physiologically acceptable cationic and acid addition salts thereof wherein $R^a$ is $CH_2OH$ or $CH_2OCH_3$;

R is a branched member selected from the group consisting of fenchyl, diisopropylcarbinyl, d-methyl-t-butylcarbinyl, d-ethyl-t-butyl-carbinyl, 2-methylthio-2,4-dimethylpentan-3-yl, di-t-butyl-carbinyl,

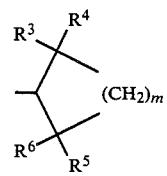 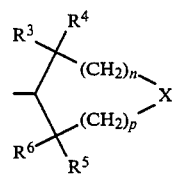

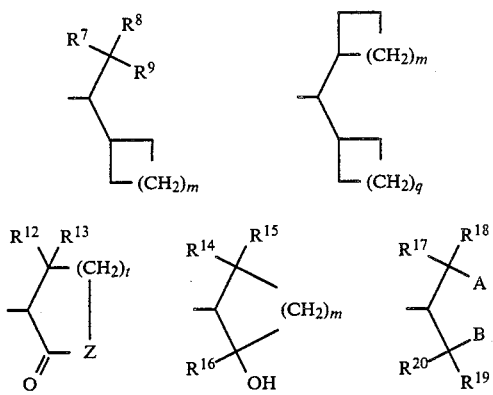

In a related patent, U.S. Pat. No. 4,411,925, Brennan, et al. disclose compounds of the above general formula with R being defined hereinabove, except $R^a$ is defined as methyl, ethyl, n-propyl or isopropyl.

U.S. Pat. No. 4,375,430 to Sklavounos discloses dipeptide sweeteners which are aromatic sulfonic acid salts of L-aspartyl-D-alaninoamides or L-aspartyl-D-serinamides.

European Patent Application No. 95772 to Tsau describe aspartyl dipeptide sweeteners of the formula:

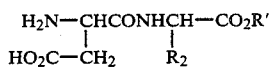

wherein R' is alkyl of 1 to 6 carbons, and $R_2$ is phenyl, phenylakylenyl or cyclohexylalkenyl, wherein the alkenyl group has 1 to 5 carbons. Closely related is U.S. Pat. No. 4,439,460 to Tsau, et al. which describes dipeptide sweeteners of the formula:

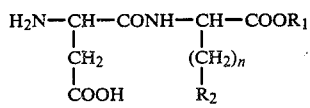

wherein n is an integer from 0 to 5, and $R_1$ is an alkyl, alkylaryl or alicyclic radical. Similar such compounds are described in many related patents, the major difference being the definition of $R_2$.

In U.S. Pat. No. 3,978,034 to Sheehan, et al., $R_2$ is defined as cycloalkenyl or phenyl. U.S. Pat. No. 3,695,898 to Hill defines $R_2$ as a mono- or a di-unsaturated alicyclic radical. Haas, et al. in U.S. Pat. No. 4,029,701 define $R_2$ as phenyl, lower alkyl or substituted or unsubstituted cycloalkyl, cycloalkenyl or cycloalkdienyl, or $S(O)_m$ lower alkyl provided that n is 1 or 2 and m is 0 or 2. Closely related are U.S. Pat. Nos. 4,448,716, 4,153,737, 4,031,258, 3,962,468, 3,714,139, 3,642,491, and 3,795,746.

U.S. Pat. No. 3,803,223 to Mazur, et al. describe dipeptide sweeteners and anti-inflammatory agents having the formula:

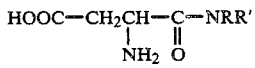

wherein R is hydrogen or a methyl radical and R' is a radical selected from the group consisting of alkyl, or

wherein Alk is a lower alkylene radical, X is hydrogen or hydroxy, and Y is a radical selected from the group consisting of cyclohexyl, naphthyl, furyl, pyridyl, indolyl, phenyl and phenoxy.

Goldkamp, et al. in U.S. Pat. No. 4,011,260 describe sweeteners of the formula:

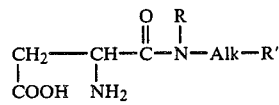

wherein R is hydrogen or a lower alkyl radical, Alk is a lower alkylene radical and R' is a carbocyclic radical. Closely related is U.S. Pat. No. 3,442,431.

U.S. Pat. No. 4,423,029 to Rizzi describes sweeteners of the formula:

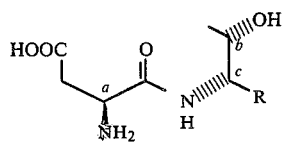

wherein R is $C_4$-$C_9$ straight, branched or cyclic alkyl, and wherein carbons a, b and c have the (S) configuration.

European Patent Application No. 48,051 describes dipeptide sweeteners of the formula:

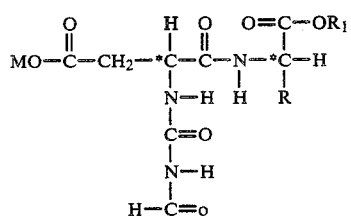

wherein
M represents hydrogen, ammonium, alkali or alkaline earth,
R represents

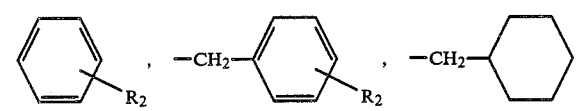

$R_1$ represents methyl, ethyl, propyl,
$R_2$ represents —OH, or $OCH_3$,
* signifies an L-optical configuration for this atom.

German Patent Application No. 7259426 discloses L-aspartyl-3-fenchylalanine methyl ester as a sweetening agent.

U.S. Pat. No. 3,971,822 to Chibata, et al., disclose sweeteners having the formula:

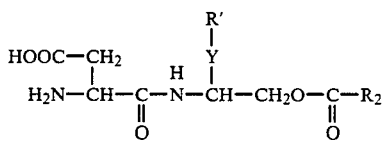

wherein R' is hydrogen or hydroxy, $R_2$ is alkyl of one to five carbon atoms, alkenyl of two to three carbon atoms, cycloalkyl of three to five carbon atoms or methyl cycloalkyl of four to six carbon atoms and Y is alkylene of one to four carbon atoms.

U.S. Pat. No. 3,907,366 to Fujino, et al. discloses L-aspartyl-aminomalonic acid alkyl fenchyl diester and its' physiologically acceptable salts as useful sweeteners. U.S. Pat. No. 3,959,245 disclose the 2-methyl cyclohexyl analog of the abovementioned patent.

U.S. Pat. No. 3,920,626 discloses N-αL-aspartyl derivatives of lower alkyl esters of O-lower-alkanoyl-L-serine, β-alanine, γ-aminobutyric acid and D-β-aminobutyric acid as sweeteners.

Miyoshi, et al. in *Bulletin of Chemical Society of Japan*, 51, p. 1433-1440 (1978) disclose compounds of the following formula as sweeteners:

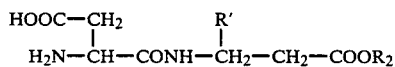

wherein R' is H, $CH_3$, $CO_2CH_3$, or benzyl and $R_2$ is lower alkyl or unsubstituted or substituted cycloalkyl.

European Patent Application No. 128,654 describes gem-diaminoalkane sweeteners of the formula:

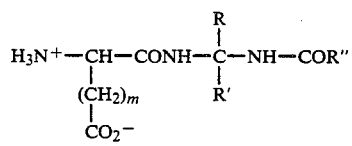

wherein m is 0 or 1, R is lower alkyl (substituted or unsubstituted), R' is H or lower alkyl, and R" is a branched alkyl, alkylcycloalkyl, cycloalkyl, polycycloalkyl, phenyl, or alkyl-substituted phenyl, and physically acceptable salts thereof.

U.S. Pat. No. 3,801,563 to Nakajima, et al. disclose sweeteners of the formula:

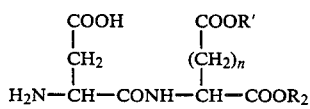

wherein R' is a branched or cyclic alkyl group of 3 to 8 carbon atoms, $R_2$ is a lower alkyl group of 1 to 2 carbon atoms and n is a integer of 0 or 1.

European Patent Application No. 34,876 describes amides of L-aspartyl-D-amino acid dipeptides of the formula:

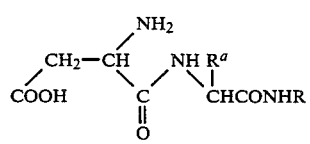

wherein $R^a$ is methyl, ethyl, n-propyl or isopropyl and R is a branched aliphatic, alicyclic or heterocyclic member which is branched at the alpha carbon atom and also branched again at one or both of the beta carbon atoms. These compounds are indicated to be of significant sweetness.

In the *Journal of Medicinal Chemistry*, 1984, Vol. 27, No. 12, pp. 1663-8, are described various sweetener dipeptide esters, including L-aspartyl-α-aminocycloalkane methyl esters.

The various dipeptide esters of the prior art have been characterized as lacking significant stability at low pH values and/or thermal stability. These characteristics have limited the scope of use of these sweeteners in food products which are of low pH values or are prepared or served at elevated temperatures.

Accordingly, it is desired to find compounds that provide quality sweetness when added to foodstuffs or pharmaceuticals at low levels and thus eliminate or greatly diminish the aforesaid disadvantages associated with prior art sweeteners.

SUMMARY OF THE INVENTION

The present new compounds are amides of certain α-aminodicarboxylic acids and aminoalkanes which are low calorie sweeteners that possess a high order of sweetness with pleasing taste and higher stability at acid pH and elevated temperatures compared to known dipeptide sweeteners.

This invention provides new sweetening compounds represented by the formula:

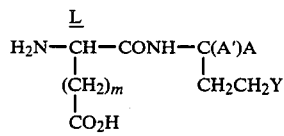    I wherein
A is hydrogen, alkyl containing 1-3 carbon atoms, hydroxyalkyl containing 1-3 carbon atoms, alkoxymethyl wherein the alkoxy contains 1-3 carbon atoms or —$CO_2R$ in which R is alkyl containing 1-3 carbon atoms;
A' is hydrogen or alkyl containing 1-3 carbon atoms;
A and A' taken together with the carbon atom to which they are attached form cycloalkyl containing 3-4 carbon atoms;
Y is —$(CHR_2)_n$—$R_1$ or —$CHR_3R_4$;
$R_1$ is alkyl-substituted cycloalkyl, cycloalkenyl, bicycloalkyl or bicycloalkenyl containing at least one alkyl in the β-position of the ring, up to 7 ring carbon atoms and up to a total of 12 carbon atoms;
$R_2$ is H or alkyl containing 1-4 carbon atoms;
$R_3$ and $R_4$ are each cycloalkyl containing 3-4 ring carbon atoms;
n=0 or 1; and
m=0 or 1;
and food-acceptable salts thereof.

DESCRIPTION OF THE PREFERRED EMBODIMENTS

In accordance with the present invention, the preferred compounds are those in which $R_1$ is an alkyl-substituted cycloalkyl or bicycloalkyl containing 5-7 ring carbon atoms and up to a total of 10 carbon atoms. Especially preferred are cycloalkyl substituted with at least one methyl group on the $\beta$ and/or $\beta'$ carbon atoms of the cycloalkyl ring. Particularly preferred cycloalkyls include cyclopropyl, cyclopentyl, and cyclohexyl and the preferred bicycloalkyl is fenchyl.

Also preferred are those compounds in which n=0. In those compounds in which n=1, $R_1$ is preferably a cyclopropyl group and $R_2$ is preferably tertiary butyl, isopropyl or cyclopropyl.

The groups representative of Y in the present new compounds include such groups as alkyl-substituted cycloalkyls, e.g., 1-methylcyclopentyl, 1-methylcyclohexyl, 1-methylcyclobutyl, 1-methylcycloheptyl, 1,2-dimethylcycloheptyl, 2,3-dimethylcyclopentyl, 2,3-dimethylcyclohexyl, 2,3-dimethylcycloheptyl, 2,4-dimethylcyclopentyl, 2,4-dimethylcyclohexyl, 2,4-dimethylcycloheptyl, 2,5-dimethylcyclopentyl, 2,5-dimethylcyclohexyl, 2,5-dimethylcycloheptyl, 2,6-dimethylcyclohexyl, 2,6-dimethylcycloheptyl, 2,7-dimethylcycloheptyl, 3,5-dimethylcyclopentyl, 4,5-dimethylcyclopentyl, 4,5-dimethylcycloheptyl, 3,6-dimethylcyclohexyl, 3,7-dimethylcycloheptyl, 4,6-dimethylcyclohexyl, 4,7-dimethylcycloheptyl, 5,6-dimethylcyclohexyl, 5,6-dimethylcyclohexyl, 5,6-dimethylcyclohexyl, 5,7-dimethylcycloheptyl, 6,7-dimethylcycloheptyl, 2,2-dimethylcyclopentyl, 2,2-dimethylcyclohexyl, 2,2-dimethylcycloheptyl, 2,2,3-trimethylcyclopentyl, 2,2,3-trimethylcyclohexyl, 2,2,3-trimethylcycloheptyl, 2,2,4-trimethylcyclopentyl, 2,2,4-trimethylcyclohexyl, 2,2,4-trimethylcycloheptyl, 2,2,5-trimethylcyclopentyl, 2,2,5-trimethylcyclohexyl, 2,2,5-trimethylcycloheptyl, 2,3,3-trimethylcyclopentyl, 2,3,3-trimethylcyclohexyl, 2,3,3-trimethylcycloheptyl, 2,4,4-trimethylcyclopentyl, 2,4,4-trimethylcyclohexyl, 2,4,4-trimethylcycloheptyl, 1,2,3-trimethylcyclopentyl, 1,2,3-trimethylcyclohexyl, 1,2,3-trimethylcycloheptyl, 1,2,4-trimethylcyclopentyl, 1,2,4-trimethylcyclohexyl, 1,2,4-trimethylcycloheptyl, 1,2,5-trimethylcyclopentyl, 1,2,5-trimethylcyclohexyl, 1,2,5-trimethylcycloheptyl, 1,2,6-trimethylcyclohexyl, 1,2,6-trimethylcycloheptyl, 1,2,7-trimethylcycloheptyl, 2,3,4-trimethylcyclopentyl, 2,3,4-trimethylcyclohexyl, 2,3,4-trimethylcycloheptyl, 2,3,5-trimethylcyclopentyl, 2,3,5-trimethylcyclohexyl, 2,3,5-trimethylcycloheptyl, 2,3,6-trimethylcyclohexyl, 2,3,6-trimethylcycloheptyl, 2,3,7-trimethylcycloheptyl, 2,2,5,5-tetramethylcyclopentyl, 2,2,5,5-tetramethylcyclohexyl, 2,2,5,5-tetramethylcycloheptyl, 2,2,6,6-tetraamethylcyclohexyl, 2,2,6,6-tetramethylcycloheptyl, 2,2,7,7-tetramethylcycloheptyl, 2,2,4,4-tetramethylcyclopentyl, 2,2,4,4-tetramethylcyclohexyl, 2,2,4,4-tetramethylcycloheptyl, 2,2,3,3-tetramethylcyclopentyl, 2,2,3,3-tetramethylcyclohexyl, 2,2,3,3-tetramethylcycloheptyl, 1,2,3,4-tetramethylcyclopentyl, 1,2,3,4-tetramethylcyclohexyl, 1,2,3,4-tetramethylcycloheptyl, 1,2,3,5-tetramethylcyclopentyl, 1,2,3,5-tetramethylcyclohexyl, 1,2,3,5-tetramethylcycloheptyl, 1,2,3,6-tetramethylcyclohexyl, 1,2,3,6-tetramethylcycloheptyl, 2,3,4,5-tetramethylcyclopentyl, 2,3,4,5-tetramethylcyclohexyl, 2,3,4,5-tetramethylcycloheptyl, 2,3,4,6-tetramethylcycloheptyl, 2,3,4,6-tetramethylcyclohexyl, 2,3,4,7-tetramethylcycloheptyl, 2,2,3,4-tetramethylcyclopentyl, 2,2,3,4-tetramethylcyclohexyl, 2,2,3,4-tetramethylcycloheptyl, 2,2,3,5-tetramethylcyclopentyl, 2,2,3,5-tetramethylcyclohexyl, 2,2,3,5-tetramethylcycloheptyl, 2,2,3,6-tetramethylcyclohexyl, 2,2,3,6-tetramethylcycloheptyl, 2,2,3,7-tetramethylcycloheptyl, 2,3,3,4-tetramethylcyclohexyl, 2,3,3,4-tetramethylcycloheptyl, 2,3,3,5-tetramethylcyclopentyl, 2,2,3,5-tetramethylcyclohexyl, 2,3,3,5-tetramethylcycloheptyl, 2,3,3,6-tetramethylcyclohexyl, 2,3,3,6-tetramethylcycloheptyl, 2,3,3,7-tetramethylcycloheptyl, 2,2,3,4-tetramethylcyclopentyl, 2,2,3,4-tetramethylcyclohexyl, 2,3,3,4-tetramethylcycloheptyl, 2,2,3,5-tetramethylcyclopentyl, 2,2,3,5-tetramethylcyclohexyl, 2,2,3,6-tetramethylcyclohexyl, 2,2,3,6-tetramethylcycloheptyl, 2,2,3,7-tetramethylcycloheptyl, 2,2,4,5-tetramethylcyclopentyl, 2,2,4,5-tetramethylcyclohexyl, 2,2,4,5-tetramethylcycloheptyl, 2,2,4,6-tetramethylcyclohexyl, 2,2,4,6-tetramethylcycloheptyl, 2,2,4,7-tetramethylcycloheptyl, dicyclopropylmethyl, t-butylcyclopropylmethyl, dicyclobutylmethyl, t-butylcyclobutylmethyl, etc.; $\beta$-alkyl-substituted cycloalkenes, e.g., 2-methyl-3-cyclohexenyl, 2-methyl-3-cyclopentenyl, 2-methyl-3-cycloheptenyl, 2-methyl-4-cycloheptenyl, 5-methyl-3-cyclopentenyl, 2-methyl-2-cyclopentenyl, 2-methyl-2-cyclohexenyl, 2-methyl-2-cycloheptenyl, 2-methyl-2-cyclopentenyl, 6-methyl-2-cyclohexenyl, 7-methyl-2-cycloheptenyl, 2,3-dimethyl-2-cyclopentenyl, 2,3-dimethyl-2-cyclohexenyl, 2,4-dimethyl-2-cyclopentenyl, 2,4-dimethyl-2-cyclohexenyl, 2,5-dimethyl-2-cyclohexenyl, 2,5-dimethyl-2-cycloheptenyl, 2,6-dimethyl-2-cyclohexenyl, 2,6-dimethyl-3-cyclohexenyl, 2,5-dimethyl-3-cyclohexenyl, 2,5-dimethyl-2-cyclopentenyl, 2,4-dimethyl-3-cyclopentenyl, 2,4-dimethyl-3-cyclohexenyl, 4,5-dimethylcyclo-3-pentenyl, 5,5-dimethyl-3-cyclopentenyl, 6,6-dimethyl-3-cyclohexenyl, 1,2-dimethyl-3-cyclopentenyl, 1,2-dimethyl-3-cyclohexenyl, 1,5-dimethyl-3-cyclopentenyl, 2,2,6-trimethyl-3-cyclohexenyl, 2,2,5-trimethyl-3-cyclohexenyl, 2,5,5-trimethyl-3-cyclohexenyl, 2,7,7,-trimethyl-3-cyclopentenyl, 2,7,7-trimethyl-4-cycloheptenyl, 2,2,7-trimethyl-3-cycloheptenyl, 2,2,7-trimethyl-4-cycloheptenyl, 2,3,6-trimethyl-3-cyclohexenyl, 2,3,7-trimethyl-3-cycloheptenyl, 2,3,5-trimethyl-3-cyclopentenyl, 2,2,6,6-tetramethyl-3-cyclohexenyl, 2,2,5,5-tetramethyl-3-cyclopentenyl, 2,2,7,7-tetramethyl-3-cycloheptenyl, 2,3,5,5-tetramethyl-3-cyclopentenyl, 2,3,6,6-tetramethyl-3-cyclohexenyl, 2,3,7,7-tetramethyl-3-cycloheptenyl, 2,3,6,6-tetramethyl-3-cycloheptenyl, 2,3,5,5-tetramethyl-3-cyclohexenyl, 2,3,4,5-tetramethyl-3-cyclopentenyl, 2,3,4,5-tetramethyl-3-cyclohexenyl, etc.; bicyclic compounds, such as norbornyl, norcaranyl, norpinanyl, bicyclo[2.2.2]octyl, etc.; alkyl substituted bicyclic compounds, e.g., 6,6-dimethyl-bicyclo[3.1.1]heptyl, 6,7,7-trimethylnorbornyl (bornyl or camphanyl), pinanyl, thujanyl, caranyl, fenchyl, 2-norbornylmethyl, etc.; unsubstituted and alkyl-substituted bicycloalkenes such as norbornenyl, norpinenyl, norcarenyl, 2-(4-norbornenyl)methyl, pinenyl, carenyl, fenchenyl, etc.; and tricyclo compounds such as adamantyl and alkyl-substituted adamantyl, etc.

The preferred $R_1$ is cycloalkyl or bicycloalkyl or alkyl-substituted cycloalkyl or bicycloalkyl, especially where the alkyl group is in the $\beta$ or $\beta'$ positions. Further, preference exists for compounds in which $R_1$ is a cycloalkyl with two, three or four alkyl groups in the $\alpha$, $\beta'$ positions such as $\beta$, $\beta$, $\beta'$, $\beta'$-tetraalkyl-substituted cyclopentyl, cyclobutyl, cyclohexyl, and cycloheptyl, as well as $\beta$, $\beta$, $\beta'$-trialkyl substituted cyclobutyl, cyclopropyl, cyclohexyl, cyclopentyl, and cycloheptyl, and fenchyl. Also preferred are $\beta$-alkylcycloalkyls in which the alkyl group is isopropyl or tertiary butyl.

These novel compounds are effective sweetness agents when used alone or in combination with other sweeteners in an ingesta, e.g., foodstuffs or pharmaceuticals. For example, other natural and/or artificial sweeteners which may be used with the novel compounds of the present invention include sucrose, fructose, corn syrup solids, dextrose, xylitol, sorbitol, mannitol, acetosulfam, thaumatin, invert sugar, saccharin, thiophene saccharin, meta-aminobenzoic acid, meta-hydroxybenzoic acid, cyclamate, chlorosucrose, dihydrochalcone, hydrogenated glucose syrups, aspartame (L-aspartyl-L-phenylalanine methyl ester) and other dipeptides, glycyrrhizin and stevioside and the like. These sweeteners when employed with the sweetness agents of the present invention, it is believed, could produce synergistic sweetness responses.

Furthermore, when the sweetness agents of the present invention are added to ingesta, the sweetness agents may be added alone or with nontoxic carriers such as the abovementioned sweeteners or other food ingredients such as acidulants and natural and artificial gums. Typical foodstuffs, and pharmaceutical preparations, in which the sweetness agents of the present invention may be used are, for example, beverages including soft drinks, carbonated beverages, ready to mix beverages and the like, infused foods (e.g. vegetables or fruits), sauces, condiments, salad dressings, juices, syrups, desserts, including puddings, gelatin and frozen desserts, like ice creams, sherbets, icings and flavored frozen desserts on sticks, confections, toothpaste, mouthwash, chewing gum, cereals, baked goods, intermediate moisture foods (e.g. dog food) and the like.

In order to achieve the effects of the present invention, the compounds described herein are generally added to the food product at a level which is effective to perceive sweetness in the food stuff and suitably is in an amount in the range of from about 0.0005 to 2% by weight based on the consumed product. Greater amounts are operable but not practical. Preferred amounts are in the range of from about 0.001 to about 1% of the foodstuff. Generally, the sweetening effect provided by the present compounds are experienced over a wide pH range, e.g. 2 to 10 preferably 3 to 7 and in buffered and unbuffered formulations.

It is desired that when the sweetness agents of this invention are employed alone or in combination with another sweetner, the sweetener or combination of sweeteners provide a sucrose equivalent in the range of from about 2 weight percent to about 40 weight percent and more preferably from about 3 weight percent to about 15 weight percent in the foodstuff or pharmaceutical.

A taste procedure for determination of sweetness merely involves the determination of sucrose equivalency. Sucrose equivalence for sweeteners are readily determined. The amount of a sweetener that is equivalent to a given weight percent sucrose can be determined by having a panel of tasters taste solutions of a sweetener at known concentrations and match its sweetness to standard solutions of sucrose.

In order to prepare compounds of the present invention, several reaction schemes may be employed. In one reaction scheme, the corresponding alkene (IV) can be reduced to the compound of formula I by reduction methods known in the art, such as by catalytic hydrogenation.

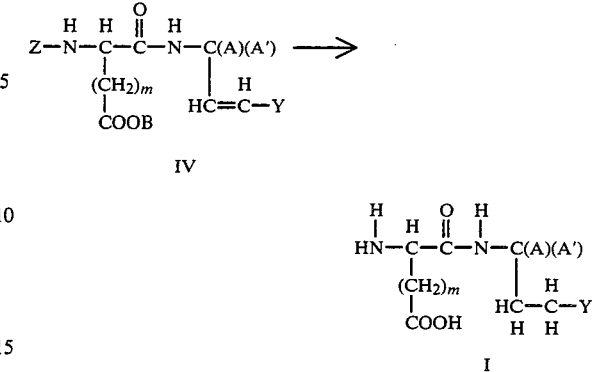

In these, Z is an amino protecting group, B is a carboxy protecting group, and A, A', Y, and n have the same meaning as previously described. A variety of protecting groups known in the art may be employed. Examples of many of these possible groups may be found in "Protective Groups in Organic Synthesis" by T. W. Green, John Wiley and Sons, 1981. Among the preferred groups that may be employed are benzyloxycarbonyl for Z and benzyl for B.

Compounds of formula IV are preferred from the condensation of compounds of general formula II (protected-amino carboxylic acid) and III (3-amino-1-propene derivatives):

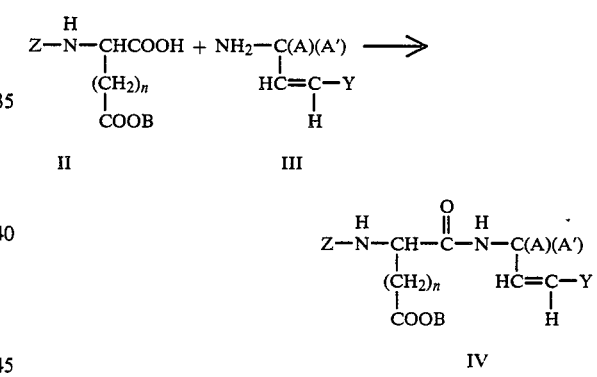

Coupling of compounds with general formula II to compounds having general formula III employs established techniques in peptide chemistry. One such technique uses dicyclohexylcarbodiimide (DCC) as the coupling agent. The DCC method may be employed with or without additives such as 4-dimethylaminopyridine or copper (II). The DCC coupling reaction generally proceeds at room temperature, however, it may be carried out from about −20° to 50° C. In a variety of solvents inert to the reactants. Thus suitable solvents include, but are not limited to, N,N-dimethyl-formamide, methylene chloride, toluene and the like. Preferably the reaction is carried out under an inert atmosphere such as argon or nitrogen. Coupling usually is complete within 2 hours but may take as long as 24 hours depending on reactants.

Various other methods can be employed to prepare the desired compounds. The following illustrates such methods using aspartic acid as the amino dicarboxylic acid.

For example, U.S. Pat. Nos. 3,786,039; 3,833,553; 3,879,372 and 3,933,781 disclose the reaction of N- protected aspartic anhydrides with amino acids and amino acid derivatives to yield the desired products. These N-protected aspartic anhydrides can be reacted with compounds of formula III by methods disclosed in the above patents. As described in U.S. Pat. No. 3,786,039 compounds of formula III can be reacted directly in inert organic solvents with L-aspartic anhydride having its amino group protected by a formyl, carbobenzyloxy, or p-methoxycarbobenzloxy group which is subsequently removed after coupling to give compounds of general formula I. The N-acyl-L-aspartic anhydrides are prepared by reacting the corresponding acids with acetic anhydride in amounts of 1.0–1.2 moles per mole of the N-acyl-L-aspartic acid at 0° to 60° C. in an inert solvent. The N-acyl-L-aspartic anhydrides are reacted with preferably 1 to 2 moles of compounds of formula III in an organic solvent capable of dissolving both and inert to the same. Suitable solvents are, but not limited to, ethyl acetate, methyl propionate, tetrahydrofuran, dioxane, ethyl ether, N,N-dimethylformamide and benzene. The reaction proceeds smoothly at 0° to 30° C. The N-acyl group is removed after coupling by catalytic hydrogenation with palladium on carbon or with HBr or HCl in a conventional manner. U.S. Pat. No. 3,879,372 discloses that this coupling method can also be performed in an aqueous solvent at a temperature of −10° to 50° C. and at a pH of 4–12.

Another method for the synthesis of the desired compounds is the reaction of compounds of formula III with suitable aspartic acid derivatives in which protecting groups have been attached to the amino and beta-carboxy groups and the alpha carboxy group has been converted to a reactive ester function. As disclosed in U.S. Pat. No. 3,475,403 these coupled products may be deprotected as described to yield the desired compounds of formula I.

An alternative scheme to the desired coupled compounds involves reaction of compounds of formula III with L-aspartic acid N-thiocarboxyanhydride by the method of Vinick and Jung, Tet. Lett., 23, 1315–18 (1982). An additional coupling method is described by T. Miyazawa, Tet. Lett., 25, 771 (1984).

Compounds of general formula III are synthesized using art recognized techniques. For example, compound of formula III can be synthesized from the dehydration of the corresponding alcohol, which was formed by reacting a Grignard reagent of formula V with an aldehyde (VI)

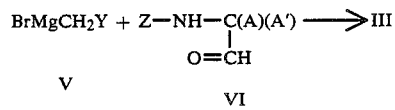

The Grignard reaction generally proceeds at 0° C., however, it may be carried out from about −200° C. to 50° C. in a variety of solvents inert to the reactants. Thus, suitable solvents include diethylether, tetrahydrofuran, and the like.

Alternatively, compound VI is reacted with the appropriate Wittig reagent under art-recognized conditions, e.g.,

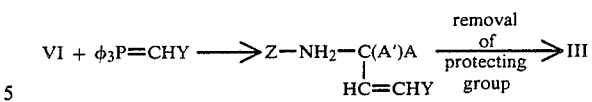

Compounds of formula (VI) are prepared by art recognized procedures from commercially available starting materials. One such method involves reacting a Wittig reagent, such methoxymethyltriphenylphosphonium chloride with a ketone, such as cyclopentanone, in the presence of a strong base, such as n-butyllithium or sec-butyllithium, to form the corresponding enol-ether, which is hydrolyzed and reduced by typical reducing agents, such as sodium borohydride to form an alcohol. The alcohol is converted to the corresponding halide, from which the Grignard reagent is derived.

The aldehyde was itself prepared from reduction of the corresponding amino acid or ester thereof. Typical reducing agents include (iso-Bu)$_2$AlH, LiAlH$_4$ and Bis(N-methylpiperazinyl) aluminum hydride. Typical temperatures for this reaction are in the range of −70° to room temperature. The reaction is carried out in solvents which are inert to both reactants and products and will dissolve both reactants. Examples include tetrahydrofuran, diethylether, methylene chloride, dimethyl formamide and the like.

In another method, compounds of formula VII can be formed from the coupling of compounds of formula II, with compounds of formula VIII:

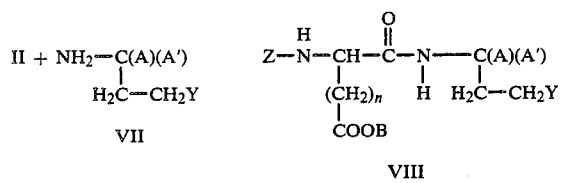

The condensation can be accomplished according to the procedure described hereinabove.

Compounds of general formula VIII can be prepared by methods known in the art. In one such method, compounds of formula III are reduced by reductive methods known in the art, e.g., catalytic hydrogenation.

With regard to the removal of protecting groups from compounds of formula IV and N-protected precursors of formula III, a number of deprotecting techniques are known in the art and can be utilized to advantage depending on the nature of the protecting groups. Among such techniques is catalytic hydrogenation utilizing palladium on carbon or transfer hydrogenation with 1,4-cyclohexadiene. Generally the reaction is carried at room temperature but may be conducted from 5° to 65° C. Usually the reaction is carried out in the presence of a suitable solvent which may include, but are not limited to water, methanol, ethanol, dioxane, tetrahydrofuran, acetic acid, t-butyl alcohol, isopropanol or mixtures thereof. The reaction is usually run at a positive hydrogen pressure of 50 psi but can be conducted over the range of 20 to 250 psi. Reactions are generally quantitative taking 1 to 24 hours for completion.

In any of the previous synthetic methods the desired products are preferably recovered from reaction mixtures by crystallization. Alternatively, normal or reverse-phase chromatography may be utilized as well as liquid/liquid extraction or other means.

The desired compounds of formula I are usually obtained in the free acid form; they may also be recovered as their physiologically acceptable salts, i.e., the corresponding amino salts such as hydrochloride, sulfate, hydrosulfate, nitrate, hydrobromide, hydroiodide, or hydrophosphate or the alkali metal salts such as the sodium potassium, lithium, or the alkaline earth metals salts such as calcium or magnesium, as well as aluminum, zinc and like salts.

Conversion of the free peptide derivatives of formula I into their physiologically acceptable salts is carried out by conventional means, as for example, bringing the compounds of formula I into contact with a mineral acid, an alkali metal hydroxide, an alkali metal oxide or carbonate or an alkaline earth metal hydroxide, oxide, carbonate or other complexed form.

These physiologically acceptable salts can also be utilized as sweetness agents usually having increased solubility and stability over their free forms.

It is known to those skilled in the art that the compounds of the present invention having asymmetric carbon atoms may exist in racemic or optically active forms. All of these forms are contemplated within the scope of the invention.

The compounds of the present invention have one asymmetric site, which is designated by an asterik (*) in the formula below, and two pseudoasymmetric sites which are designated by a double asterik (**):

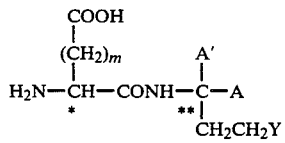

Whenever A is identical to A', the compounds of the present invention have only one assymmetric site, designated by the asterik, in the dicarboxylic acid moiety. Although both the D and L forms are possible; the preferred compounds are those in which the dicarboxylic acid group is in the L configuration. Whenever the groups A' and A are different, the carbon atom designated by the double asteriks become an asymmetric center and the compounds of the present invention will contain at least two asymmetric centers. Regardless, the configuration around each of the asymmetric sites, whenever present, may exist in either the D or L forms, and all possible stereoisomers are contemplated to be within the scope of the present invention. Since the aspartyl group is in the L-configuration, whenever an asymmetric center is present at the other carbon site, the compounds of the present invention are diasteromers, which can be separated, if desired, by art-recognized techniques, as, for example, chromatography, However, mixtures of at least any two stereoisomers exhibit sweetness properties and are useful as sweeteners.

The following examples further illustrate the invention.

EXAMPLE 1

N-(L-Aspartyl)-3-amino-1-(2,2,5,5-tetramethylcyclopentyl)butane

Methoxymethyltriphenylphosphonium chloride is suspended in tetrahydrofuran at 0° C. under argon. Sec-Butyllithium in cyclohexane is added, followed by a solution of 2,2,5,5-tetramethylcyclopentanone in tetrahydrofuran. After one hour water is added to the reaction mixture. The organic layer is separated, washed with water, dried over MgSO$_4$ and evaporated to yield the enol ether. The ether is dissolved in dioxane and 2M H$_2$SO$_4$ is added. The mixture is refluxed until the reaction is complete as shown by thin layer chromatography. The mixture is poured into water and extracted with ether. The organic layer is dried over MgSO$_4$ and evaporated to yield 2,2,5,5-tetramethylcyclopentane-1-carboxaldehyde.

2,2,5,5-Tetramethylcyclopentane-1-carboxaldehyde is dissolved in 95% ethanol and sodium borohydride is added. After 24 hours, the reaction is quenched with 1M HCl and extracted with ether. The extract is washed, dried over MgSO$_4$ and evaporated to yield 2,2,5,5-tetramethyl-1-cyclopentylmethanol.

2,2,5,5-Tetramethyl-1-cyclopentylmethanol is dissolved in benzene and stirred at 0° C. under argon. A solution of phosphorus tribromide in benzene is added and the mixture is stirred for 2 hours and then heated to 60° C. for 4 hours. The mixture is cooled, poured into ice and extracted with ether. The organic layer is washed with saturated NaHCO$_3$, dried over MgSO$_4$ and evaporated to yield 2,2,5,5-Tetramethyl-1-cyclopentylmethylbromide.

N-Boc-D-alanine is dissolved in tetrahydrofuran and stirred at 0° C. under argon. Bis(N-methylpiperazinyl)aluminum hydride is added and the reaction mixture is heated to reflux overnight. Ether is then added, and the excess hydride is quenched with saturated NaCl. The aqueous phase is separated and extracted with ether. The combined organic phases are washed with 2M NaOH, 2M HCl and saturated NaCl. The solution is dried over Na$_2$SO$_4$ and evaporated to yield N-Boc-D-alaninal.

A solution of 2,2,5,5-Tetramethyl-1-cyclopentylmethyl bromide in ether is added slowly to magnesium turnings until the Grignard reagent begins to form. The remainder of the alkyl bromide is then added and the mixture stirred until all the magnesium has dissolved. At 0° C. a solution of N-Boc-D-alaninal is then added and the mixture is stirred overnight. The reaction is quenched with 1M HCl, extracted with ether and the extracts are evaporated. The residue is dissolved in dioxane and 2M H$_2$SO$_4$ is added. The mixture is heated until the alcohol is dehydrated, as shown by thin layer chromatography. Water is added and the mixture is extracted with ether. The organic layer is dried over MgSO$_4$ and evaporated to give N-Boc-2-amino-4-(2,2,5,5-tetramethyl-1-cyclopentyl)-3-butene.

N-Boc-2-amino-4-(2,2,5,5-tetramethyl-1-cyclopentyl)-3-butene is dissolved in trifluoroacetic acid and the solution is stirred overnight. Water is added and the mixture is made basic with 20% KOH. The mixture is extracted with ether, and the organic layer is dried over Na$_2$SO$_4$ and evaporated to yield 2-amino-4-(2,2,5,5-tetramethyl-1-cyclopentyl)-3-butene.

To a magnetically stirred solution of 2-amino-4-(2,2,5,5-tetramethyl-1-cyclopentyl)-3-butene in dry dimethylformamide at 0° C. under argon atmosphere is added N-Cbz-L-aspartic acid beta-benzyl ester followed by copper (II) chloride and dicyclohexylcarbodiimide. This is stirred for 18 hours, after which the reaction mixture is poured into 0.1N HCl and extracted with ethyl acetate. The organic phase is washed with saturated NaHCO$_3$ and then water, and dried over MgSO$_4$. Evaporation of the solvent yields N-(N'-Cbz-L-Aspartyl beta-benzyl ester)-2-amino-4-(2,2,5,5-tetramethyl-1-cyclopentyl)-3-butene.

N-(N'-Cbz-L-Aspartyl beta-benzyl ester)-2-amino-4-(2,2,5,5-tetramethyl-1-cyclopentyl)-3-butene is dissolved in $CH_3OH$ and hydrogenated over 5% Pd/C in a Paar apparatus. Upon completion of the reaction the mixture is filtered and concentrated to yield the final product.

Similarly, by utilizing the appropriate starting materials, the following additional dipeptides are also prepared:

N-L-aspartyl-3-amino-1-(2,2,5-trimethylcyclopentyl)butane.
N-L-aspartyl-3-amino-1-(2,5-dimethylcyclopentyl)butane.
N-L-aspartyl-3-amino-1-(dicyclopropylmethyl)butane.
N-L-aspartyl-3-amino-1-(fenchyl)butane.
N-L-aspartyl-3-amino-1-(2-t-butylcyclopentyl)butane.
N-L-aspartyl-3-amino-1-(1-t-butyl-1-cyclopropylmethyl)butane.
N-L-aspartyl-3-amino-1-(1-isopropyl-1-cyclopropylmethyl)butane.

EXAMPLE 2

N-(L-Aspartyl)-3-amino-3-methyl-1-(2,2,5,5-tetramethyl-1-cyclopentyl)butane

Methoxymethyltriphenylphosphonium chloride is suspended in tetrahydrofuran at 0° C. under argon. Sec-Butyllithium in cyclohexane is added, followed by a solution of 2,2,5,5-tetramethylcyclopentanone in tetrahydrofuran. After one hour water is added to the reaction mixture. The organic layer is separated, washed with water, dried over $MgSO_4$ and evaporated to yield the enol ether. The ether is dissolved in dioxane and 2M $H_2SO_4$ is added. The mixture is refluxed until the reaction is complete as shown by thin layer chromatography. The mixture is poured into water and extracted with ether. The organic layer is dried over $MgSO_4$ and evaporated to yield 2,2,5,5-tetramethylcyclopentane-1-carboxaldehyde.

2,2,5,5-Tetramethylcyclopentane-1-carboxaldehyde is dissolved in 95% ethanol and sodium borohydride is added. After 24 hours, the reaction is quenched with 1M HCl and extracted with ether. The extract is washed, dried over $MgSO_4$ and evaporated to yield 2,2,5,5-tetramethyl-1-cyclopentylmethanol.

2,2,5,5-Tetramethyl-1-cyclopentylmethanol is dissolved in benzene and stirred at 0° C. under argon. A solution of phosphorus tribromide in benzene is added and the mixture is stirred for 2 hours and then heated to 60° C. for 4 hours. The mixture is cooled, poured into ice and extracted with ether. The organic layer is washed with saturated $NaHCO_3$, dried over $MgSO_4$ and evaporated to yield 2,2,5,5-Tetramethyl-1-cyclopentylmethyl bromide.

N-Boc-2-aminoisobutyric acid is dissolved in tetrahydrofuran and stirred at 0° C. under argon. Bis(N-methylpiperazinyl)aluminum hydride is added and the reaction mixture heated to reflux overnight. Ether is then added, and the excess hydride is quenched with saturated NaCl. The aqueous phase is separated and extracted with ether. The combined organic phases are washed with 2M NaOH, 2M HCl and saturated NaCl. The solution is dried over $NaSO_4$ and evaporated to yield N-Boc-2-amino-2-methylpropanal.

A solution of 2,2,5,5-Tetramethyl-1-cyclopentylmethyl bromide in ether is added slowly to magnesium turnings until the Grignard reagent begins to form. The remainder of the alkyl bromide is then added and the mixture is stirred until all of the magnesium has dissolved. At 0° C. a solution of N-Boc-2-amino-2-methylpropanal is then added and the mixture is stirred overnight. The reaction is quenched with 1M HCl, extracted with ether and the extracts are evaporated. The residue dissolves in dioxane and 2M $H_2SO_4$ is added. The mixture is heated until the alcohol is dehydrated as shown by thin layer chromatography. Water is added and the mixture extracted with ether. The organic layer is dried over $MgSO_4$ and evaporated to give N-Boc-2-amino-2-methyl-4-(2,2,5,5-tetramethyl-1-cyclopentyl)butene.

N-Boc-2-amino-2-methyl-4-(2,2,5,5-tetramethyl-1-cyclopentyl)butene is dissolved in trifluoroacetic acid and the solution is stirred overnight. Water is added and the mixture made basic with 20% KOH. The mixture is extracted with ether, the organic layer dried over $NaSO_4$ and evaporated to yield 2-amino-2-methyl-4-(2,2,5,5-tetramethyl-1-cyclopentyl)butene.

To a magnetically stirred solution of 2-amino-2-methyl-4-(2,2,5,5-tetramethyl-1-cyclopentyl)butene in dry dimethylformamide at 0° C. under argon atmosphere is added N-Cbz-L-aspartic acid beta-benzyl ester followed by copper (II) chloride and dicyclohexylcarbodiimide. This is stirred for 18 hours, after which the reaction mixture is poured into 0.1N HCl and extracted with ethyl acetate. The organic phase is washed with saturated $NaHCO_3$ and then water, and is dried over $MgSO_4$. Evaporation of the solvent yields N-(N'-Cbz-L-Aspartyl beta-benzyl ester)-2-amino-2-methyl-4-(2,2,5,5-tetramethyl-1-cyclopentyl)-butene.

N-(N'-Cbz-L-Aspartyl beta-benzyl ester)-2-amino-2-methyl-4-(2,2,5,5-tetramethyl-1-cyclopentyl)butene is dissolved in $CH_3OH$ and hydrogenated over 5% Pd/C in a Paar apparatus. Upon completion of the reaction the mixture is filtered and concentrated to yield the final product.

Similarly, by utilizing the appropriate starting materials, the following additional dipeptides are also prepared:

N-L-aspartyl-3-amino-3-methyl-1-(2,2,5-trimethylcyclopentyl)butane.
N-L-aspartyl-3-amino-3-methyl-1-(2,5-diemthylcyclopentyl)butane.
N-L-aspartyl-3-amino-3-methyl-1-(dicyclopropylmethyl)butane.
N-L-aspartyl-3-amino-3-methyl-1-(fenchyl)butane.
N-L-aspartyl-3-amino-3-methyl-1-(2-t-butylcyclopentyl)butane.
N-L-aspartyl-3-amino-3-methyl-1-(1-t-butyl-1-cyclopropylmethyl)butane.
N-L-aspartyl-3-amino-3-methyl-1-(1-isopropyl-1-cyclopropylmethyl)butane.

EXAMPLE 3

N-(L-Aspartyl)-1-amino-1-[2-(2,2,5,5-tetramethyl-1-cyclopentyl)ethyl]cyclopropane Methoxymethyltriphenylphosphonium chloride is suspended in tetrahydrofuran at 0° C. under argon. Sec-Butyllithium in cyclohexane is added, followed by a solution of 2,2,5,5-tetramethylcyclopentanone in tetrahydrofuran. After one hour water is added to the reaction mixture. The organic layer is separated, washed with water, dried over $MgSO_4$ and evaporated to yield the enol ether. The ether is dissolved in dioxane and 2M $H_2SO_4$ is added. The mixture is refluxed until the reaction is complete as shown by thin layer chromatography. The mixture is poured into water and extracted with ether. The organic layer is dried over MgSO$_4$ and evaporated to yield 2,2,5,5-tetramethylcyclopentane-1-carboxaldehyde.

2,2,5,5-Tetramethylcyclopentane-1-carboxaldehyde is dissolved in 95% ethanol and sodium borohydride is added. After 24 hours, the reaction is quenched with 1M HCl and extracted with ether. The extract is washed, dried over MgSO$_4$ and evaporated to yield 2,2,5,5-tetramethyl-1-cyclopentylmethanol.

2,2,5,5-Tetramethyl-1-cyclopentylmethanol is dissolved in benzene and stirred at 0° C. under argon. A solution of phosphorus tribromide in benzene is added and the mixture is stirred for 2 hours and then heated to 60° C. for 4 hours. The mixture is cooled, poured into ice and extracted with ether. The organic layer is washed with saturated NaHCO$_3$, dried over MgSO$_4$ and evaporated to yield 2,2,5,5-Tetramethyl-1-cyclopentylmethyl bromide.

N-Boc-1-amino-1-cyclopropanecarboxylic acid is dissolved in tetrahydrofuran and stirred at 0° C. under argon. Bis(N-methylpiperazinyl)aluminum hydride is added and the reaction mixture is heated to reflux overnight. Ether is then added, and the excess hydride is quenched with saturated NaCl. The aqueous phase is separated and extracted with ether. The combined organic phases are washed with 2M NaOH, 2M HCl and saturated NaCl. The solution is dried over Na$_2$SO$_4$ and evaporated to yield N-Boc-1-amino-1-cyclopropanecarboxaldehyde.

A solution of 2,2,5,5-Tetramethyl-1-cyclopentylmethyl bromide in ether is added slowly to magnesium turnings until the Grignard reagent begins to form. The remainder of the alkyl bromide is then added and the mixture is stirred until all the magnesium dissolves. At 0° C. a solution of N-Boc-1-amino-1-cyclopropanecarboxaldehyde is then added and the mixture is stirred overnight. The reaction is quenched with 1M HCl, extracted with ether and the extracts are evaporated. The residue is dissolved in dioxane and 2M H$_2$SO$_4$ is added. The mixture is heated until the alcohol is dehydrated, as shown by thin layer chromatography. Water is added and the mixture is extracted with ether. The organic layer is dried over MgSO$_4$ and evaporated to give N-Boc-1-amino-1-(2,2,5,5-tetramethyl-1-cyclopentyl)ethenylcyclopropane.

N-Boc-1-amino-1-(2,2,5,5-tetramethyl-1-cyclopentyl)ethenylcyclopropane is dissolved in trifluoroacetic acid and the solution is stirred overnight. Water is added and the mixture is made basic with 20% KOH. The mixture is extracted with ether, and the organic layer is dried over Na$_2$SO$_4$ and is evaporated to yield 1-amino-1-(2,2,5,5-tetramethyl-1-cyclopentyl)ethenylcyclopropane.

To a magnetically stirred solution of 1-amino-1-(2,2,5,5-tetramethyl-1-cyclopentyl)ethenylcyclopropane in dry dimethylformamide at 0° C. under argon atmosphere is added N-Cbz-L-aspartic acid beta-benzyl ester followed by copper (II) chloride and dicyclohexylcarbodiimide. This is stirred for 18 hours, after which the reaction mixture is poured into 0.1N HCl and extracted with ethyl acetate. The organic phase is washed with saturated NaHCO$_3$ and then water, and dried over MgSO$_4$. Evaporation of the solvent yields N-(N'-Cbz-L-Aspartyl beta-benzyl ester)-1-amino-1-(2,2,5,5-tetramethyl-1-cyclopentyl)ethenylcyclopropane.

N-(N'-Cbz-L-Aspartyl beta-benzyl ester)-1-amino-1-(2,2,5,5-tetramethyl-1-cyclopentyl)ethenylcyclopropane is dissolved in absolute ethanol at 0° C. in an ultrasound bath. Palladium on carbon (10%) is added. The hydrogen source, 1,4-cyclohexadiene, is added, and ultrasound is commenced for eight minutes. The slurry is then filtered through a bed of Celite with ethyl alcohol. Rotary evaporation affords the final product.

Similarly, by utilizing the appropriate starting materials, the following additional dipeptides are prepared:
N-L-aspartyl-1-amino-1-[2-(2,2,5,-trimethylcyclopentyl)ethyl]cyclopropane.
N-L-aspartyl-1-amino-1-[2-(2,5-dimethylcyclopentyl)ethyl]cyclopropane.
N-L-aspartyl-1-amino-1-[2-(2-dicyclopropylmethyl)ethyl]cyclopropane.
N-L-aspartyl-1-amino-1-[2-(fenchyl)ethyl]cyclopropane.
N-L-aspartyl-1-amino-1-[2-(2-t-butylcyclopentyl)ethyl]cyclopropane.
N-L-aspartyl-1-amino-1-[2-(1-t-butyl-1-cyclopropylmethyl)ethyl]cyclopropane.
N-L-aspartyl-1-amino-1-[2-(1-isopropyl-1-cyclopropylmethyl)ethyl]cyclopropane.

EXAMPLE 4

N-L-Aspartyl-4-hydroxy-3-amino-1-(2,2,5,5-tetramethylcyclopentyl)butane

Methoxymethyltriphenylphosphonium chloride is suspended in tetrahydrofuran at 0° C. under argon. Sec-Butyllithium in cyclohexane is added, followed by a solution of 2,2,5,5-tetramethylcyclopentanone in tetrahydrofuran. After one hour water is added to the reaction mixture. The organic layer is separated, washed with water, dried over MgSO$_4$ and evaporated to yield the enol ether. The ether is dissolved in dioxane and 2M H$_2$SO$_4$ is added. The mixture is refluxed until the reaction is complete as shown by thin layer chromatography. The mixture is poured into water and extracted with ether. The organic layer is dried over MgSO$_4$ and evaporated to yield 22,5,5-tetramethylcyclopentane-1-carboxaldehyde.

2,2,5,5-Tetramethylcyclopentane-1-carboxaldehyde is dissolved in 95% ethanol and sodium borohydride is added. After 24 hours, the reaction is quenched with 1M HCl and extracted with ether. The extract is washed, dried over MgSO$_4$ and evaporated to yield 2,2,5,5-tetramethyl-1-cyclopentylmethanol.

2,2,5,5-Tetramethyl-1-cyclopentylmethanol is dissolved in benzene and stirred at 0° C. under argon. A solution of phosphorus tribromide in benzene is added and the mixture is stirred for 2 hours and then heated to 60° C. for 4 hours. The mixture is cooled, poured into ice and extracted with ether. The organic layer is washed with saturated NaHCO$_3$, dried over MgSO$_4$ and evaporated to yield 2,2,5,5-Tetramethyl-1-cyclopentylmethyl bromide.

N-CBZ-D-serine methyl ester is dissolved in toluene and 2 equivalents of dihydropyran. 0.1 equivalents of para-toluene-sulfonic acid is added and the contents of the flask are stirred overnight at room temperature. The solvents are removed under vacuum to give a paste. The paste is dissolved in ethyl acetate and washed with dilute sodium hydrogen carbonate. The organic phase is dried and evaporated to give N-CBZ-D-serine-methyl ester-O-tetrahydropyran.

The toluene solution is cooled to −78° C. and 2.2 equivalents of di-isobutyl aluminum hydride is added through a syringe. The solution is stirred for six hours at −78° C. TLC shows loss of starting material. The contents of the flask are quenched with 10% aqueous citric acid and extracted with ethyl acetate. The organic layer is dried and evaporated to give N-CBZ-D-serinal-O-tetrahydropyran.

Triphenylphosphine is suspended in toluene. 2,2,5,5-tetramethyl cyclopentyl methyl bromide is added and the reaction is refluxed. The mixture is cooled and the phosphonium salt is collected by vacuum filtration.

The 2,2,5,5-tetramethyl cyclopentylmethyl triphenylphosphonium chloride is suspended in tetrahydrofuran at 0° C. under argon. Sec-Butyllithium in cyclohexane is added followed by a solution of N-CBZ-D-serinal-O-tetrahydropyran in tetrahydrofuran. After one hour, water is added to the reaction mixture. The organic layer is separated, washed with water, dried over $MgSO_4$ and evaporated to afford 3-amino-4-O-THF-1-(2,2,5,5-tetramethylcyclopentyl)-1-butene.

To a magnetically stirred solution of the above product in dry dimethylformamide at 0° C. under argon is added N-Cbz-L-aspartic acid beta-benzyl ester followed by copper (II) chloride and dicyclohexylcarbodiimide. This is stirred for 18 hours, after which the reaction mixture is poured into 0.1N HCl and extracted with ethyl acetate. The organic phase is washed with saturated $NaHCO_3$ and then water, and dried over $MgSO_4$. Evaporation of the solvent yields N-(N'-Cbz-L-Aspartyl beta-benzyl ester)-3-amino-4-hydroxy-1-(2,2,5,5-tetramethylcyclopentyl)-1-butene.

The above product is dissolved in $CH_3OH$ and hydrogenated over 5% Pd/C in a Paar apparatus. Upon completion of the reaction, the mixture is filtered and concentrated to yield the final product.

Similarly, by using the appropriate starting materials, the following additional compounds are prepared:

N-L-aspartyl-4-hydroxy-3-amino-1-(2,2,5-trimethylcyclopentyl)butane.
N-L-aspartyl-4-hydroxy-3-amino-1-(2,5-dimethylcyclopentyl)butane.
N-L-aspartyl-4-hydroxy-3-amino-1-(dicyclopropylmethyl)butane.
N-L-aspartyl-4-hydroxy-3-amino-1-(fenchyl)butane.
N-L-aspartyl-4-hydroxy-3-amino-1-(2-t-butylcyclopentyl)butane.
N-L-aspartyl-4-hydroxy-3-amino-1-(1-t-butyl-1-cyclopropylmethyl)butane.
N-L-aspartyl-4-hydroxy-3-amino-1-(1-isopropyl-1-cyclopropylmethyl)butane.

EXAMPLE 5

N-L-Aspartyl-2-amino-4-(2,2,5,5-tetramethylcyclopentyl)butanoic methyl ester

Methoxymethyltriphenylphosphonium chloride is suspended in tetrahydrofuran at 0° C. under argon. Sec-Butyllithium in cyclohexane is added, followed by a solution of 2,2,5,5-tetramethylcyclopentanone in tetrahydrofuran. After one hour water is added to the reaction mixture. The organic layer is separated, washed with water, dried over $MgSO_4$ and evaporated to yield the enol ether. The ether is dissolved in dioxane and 2M $H_2SO_4$ is added. The mixture is refluxed until the reaction is complete as shown by thin layer chromatography. The mixture is poured into water and extracted with ether. The organic layer is dried over $MgSO_4$ and evaporated to yield 2,2,5,5-tetramethylcyclopentane-1-carboxaldehyde.

2,2,5,5-Tetramethylcyclopentane-1-carboxaldehyde is dissolved in 95% ethanol and sodium borohydride is added. After 24 hours, the reaction is quenched with 1M HCl and extracted with ether. The extract is washed, dried over $MgSO_4$ and evaporated to yield 2,2,5,5-tetramethyl-1-cyclopentylmethanol.

2,2,5,5-Tetramethyl-1-cyclopentylmethanol is dissolved in benzene and stirred at 0° C. under argon. A solution of phosphorus tribromide in benzene is added and the mixture is stirred for 2 hours and then heated to 60° C. for 4 hours. The mixture is cooled, poured into ice and extracted with ether. The organic layer is washed with saturated $NaHCO_3$, dried over $MgSO_4$ and evaporated to yield 2,2,5,5-Tetramethyl-1-cyclopentylmethyl bromide.

Dibenzyl malonate (10.0 g, 35.2 mmol) was taken up in 1,4-dioxane (100 mL) and treated with a 40% aqueous solution of acetic acid (35 mL), followed by the slow addition (2.5 h) of solid sodium nitrite (10 g). The reaction was stirred for another 2.5 hours and extracted into ether (3×70 mL). The organic phase was washed with a 1% solution of $NaHCO_3$ until the aqueous layer was slightly acidic (pH 5–6). The ethereal solution was dried over $MgSO_4$ and removed under reduced pressure to give an oil (10.9 g). The crude oxime was carried directly to the next step.

Amalgamated aluminum (obtained from 1.25 g, 0.463 g atom of aluminum foil) was covered with tetrahydrofuran (28 mL), followed by 1.9 mL of water. The reaction mixture was stirred mechanically and cooled in a dry ice acetone bath. A solution of the crude oxime (from the previous step) in 30 mL of tetrahydrofuran was added dropwise (20 min.) while the temperature was maintained between −15° and −30° C. The ice bath was removed and a spontaneous reaction occurred, which resulted in a rapid rise in temperature (50° C.) When the evolution of heat ceased, the mixture was refluxed for 1 hour, diluted with ether (100 mL), and filtered through Celite. The solvent was removed under reduced pressure to give the crude amine (7.5 g), which was taken to the following step without further purification.

A small sample (0.5 g) of the crude amine was taken up in dry ether (10 mL) and treated with HCl gas at 0° C. The amine hydrochloride was collected by filtration, washed with ether, dried in vacuo, and recrystallized from MeOH/i-$Pr_2O$.

The crude amine (7 g) is dissolved in a saturated solution of $NaHCO_3$ (200 mL) and cooled in an ice bath. Benzyl chloroformate (4.0 g, 23 mmol) is added dropwise (0.5 h) to the vigorously stirred solution. The reaction mixture is left at room temperature for 12 hours, during which time the product precipitates. The product is collected by filtration, washed with water, dried in air, and recrystallized from i-PrOH: yield 4.8 g (52%), from dibenzyl malonate.

The above product is dissolved in acetone/water (4:1, 133 mL). The solution is stirred and lithium hydroxide monohydrate (0.42 g, 10 mmol) in water (11 mL) is added dropwise (1 h). The reaction mixture is stirred for 12 hours at room temperature, the acetone is removed under reduced pressure, and the residue is taken up into a saturated solution of $NaHCO_3$ (60 mL) and extracted with EtOAc (3×100 mL). The EtOAc washings are combined, dried over $MgSO_4$, and removed under reduced pressure to give a solid, which is crystallized from EtOAc/hexane. This solid is identified as recovered starting material (1.1 g, 25.4%). The aqueous phase is acidified with 3N HCl to pH≃1 and extracted with CHCl₃(4×50 mL). The combined CHCl₃ washings are dried over MgSO₄, and the solvent is removed under reduced pressure to give a residue which is crystallized from i-ProH to afford N-Cbz-aminomalonic acid monobenzyl ester.

The above product is dissolved in tetrahydrofuran and stirred at 0° C. under argon. Bis(N-methylpiperazinyl)aluminum hydride is added and the reaction mixture is heated to reflux overnight. Ether is then added and the excess hydride is quenched with saturated NaCl. The combined organic phases are washed with 2M NaOH₃ in 2M HCl and saturated NaCl. The solution is dried over Na₂SO₄ and evaporated to yield the 2-benzyloxycarbonyl-2-CBZ-aminoacetaldehyde.

Triphenylphosphine is suspended in toluene. 2,2,5,5-tetramethylcyclopentyl methyl bromide is added and the reaction is refluxed. The mixture is cooled and the phosphonium salt is collected by vacuum filtration.

The 2,2,5,5-tetramethyl cyclopentylmethyl triphenylphosphonium bromide is suspended in tetrahydrofuran at 0° C. under argon. Sec-Butyllithium in cyclohexane is added followed by a solution of 2-benzyloxycarbonyl-2CBZ-aminoacetaldehyde in tetrahydrofuran. After one hour, water is added to the reaction mixture. The organic layer is separated, washed with water and dried over MgSO₄ and evaporated to yield the alkene, benzyl 2-CBZ-amino-4-(2,2,5,5-tetramethylcyclopentyl)-3-butenoate.

The above product is dissolved in absolute alcohol at 0° C. in an ultrasound bath. Palladium on carbon is added. The hydrogen source, 1,4-cyclohexadiene is added and ultrasound is commenced for eight minutes. The slurry is then filtered through a bed of Celite with ethyl alcohol. The solvent is removed to afford 2-amino-4-(2,2,5,5-tetramethylcyclopentyl)but-3-enoic acid.

The above product is dissolved in ether and is reacted with diazomethane (which is generated in situ from N-Nitrosomethyl urea and potassium hydroxide) at 5° C. and under N₂. The ether is evaporated to afford the methyl 2-amino-4-(tetramethylcyclopentyl)-3-butenoate.

To a magnetically stirred solution of the above product in dry dimethylformamide at 0° C. under argon is added N-Cbz-L-aspartic acid beta-benzyl ester followed by copper (II) chloride and dicyclohexylcarbodiimide. This is stirred for 18 hours, after which the reaction mixture is poured into 0.1N HCl and extracted with ethyl acetate. The organic phase is washed with saturated NaHCO₃ and then water, and dried over MgSO₄. The solvent is evaporated.

The newly formed methyl ester is coupled with N-CBZ-L-aspartic acid beta-benzyl ester and hydrogenated as described in Example 4 to afford the final product.

Similarly, by using the appropriate starting materials, the following additional compounds are prepared:

N-L-aspartyl-2-amino-4-(2,2,5-trimethylcyclopentyl)-butanoic acid methyl ester.
N-L-aspartyl-2-amino-4-(2,5-dimethylcyclopentyl)-butanoic acid methyl ester.
N-L-aspartyl-2-amino-4-(dicyclopropylmethyl)-butanoic acid methyl ester.
N-L-aspartyl-2-amino-4-(fenchyl)butanoic acid methyl ester.
N-L-aspartyl-2-amino-4-(2-t-butylcyclopentyl)butanoic acid methyl ester.
N-L-aspartyl-2-amino-4-(1-t-butyl-1-cyclopropylmethyl)butanoic acid methyl ester.
N-L-aspartyl-2-amino-4-(1-isopropyl-1-cyclopropylmethyl)butanoic acid methyl ester.

The compounds of the present invention possess higher sweetness and/or stability in comparison with comparable compounds of the prior art.

For example, in present experience, the present new compounds wherein A is carbalkoxy are substantially sweeter than aspartame, the present commercially-used synthetic dipeptide sweetner.

Compounds wherein A and A' are other than carbalkoxy are of substantially higher stability to acid pH and exhibit a substantially higher thermal stability. However, some of these compunds may be of the same order of sweetness as aspartame with others being of a higher order of sweetness. In general, the most preferred compounds are those which exhibit an order of sweetness which is at least about twice that of aspartame.

In particular, compounds in which A is carbalkoxy and Y is an alkyl substituted cycloalkyl, especially a β-methyl-substituted cycloalkyl as defined herein, are of significantly higher order of sweetness, and, in many cases, of a higher stability (pH and thermal) than aspartame.

In present experience, the order of sweetness in terms of the A and A' substituents with each definition of Y is as follows:

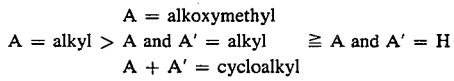

The order of stability of the present compounds, with each definition of Y, in terms of A and A' is as follows:

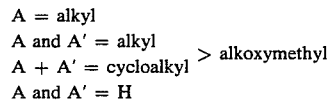

There, of course, can be minor variation in the stability and/or sweetness in any particular combination of Y groups and A and A' groups but the foregoing represents the general stability and sweetness properties of the present compounds.

What is claimed is:

1. A compound represented by the formula

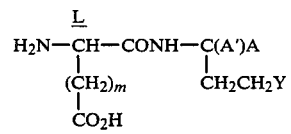

wherein
A is —CO₂R in which R is alkyl containing 1-3 carbon atoms;
A' is hydrogen or alkyl containing 1-3 carbon atoms;
Y is —(CHR₂)ₙ—R₁ or —CHR₃R₄;
R₁ is alkyl-substituted cycloalkyl, or, bicycloalkyl containing at least one alkyl in the β-position of the ring, containing up to 7 ring carbon atoms and up to a total of 12 carbon atoms;
R₂ is H or alkyl containing 1-4 carbon atoms;

R₃ and R₄ are each cycloalkyl containing 3–4 ring carbon atoms;
n=0 or 1; and
m=0 or 1;
and food-acceptable salts thereof.

2. A compound according to claim 1 wherein $R_1$ is cyclopentyl or cyclohexyl containing a total of up to 10 carbon atoms.

3. A compound according to claim 1 wherein n=0.

4. A compound according to claim 1 wherein $R_1$ is mono-, di-, tri- or tetramethyl cycloalkyl or bicycloalkyl containing up to 10 carbon atoms.

5. A compound according to claim 4 wherein $R_1$ is a β-methyl-substituted cycloalkyl or bicycloalkyl.

6. A compound according to claim 4 wherein $R_1$ is a β,β, or β,β-dimethyl-substituted cycloalkyl or bicycloalkyl.

7. A compound according to claim 4 wherein $R_1$ is a β,β,β'-trimethyl-substituted cycloalkyl or bicycloalkyl.

8. A compound according to claim 4 wherein $R_1$ is a β,β,β',β'-tetramethyl-substituted cycloalkyl or bicycloalkyl.

9. A compound according to claim 1 wherein $R_3$ and $R_4$ are cyclopropyl.

10. The compound according to claim 1 which is N-L-aspartyl 2-amino-4-(2,2,5,5-tetramethylcyclopentyl)butanoic acid methyl ester.

11. The compound according to claim 1 which is N-L-aspartyl 2-amino-4-(2,2,5-trimethylcyclopentyl)butanoic acid methyl ester.

12. The compound according to claim 1 which is N-L-aspartyl 2-amino-4-(2,5-dimethylcyclopentyl)butanoic acid methyl ester.

13. The compound according to claim 1 which is N-L-aspartyl 2-amino-4-(dicyclopropylmethyl)butanoic acid methyl ester.

14. The compound according to claim 1 which is N-L-aspartyl 2-amino-4-(fenchyl)butanoic acid methyl ester.

15. The compound according to claim 1 which is N-L-aspartyl 2-amino-4-(2-t-butylcyclopentyl)butanoic acid methyl ester.

16. The compound according to claim 1 which is N-L-aspartyl 2-amino-4-(1-t-butyl-1-cyclopropylmethyl)butanoic acid methyl ester.

17. The compound according to claim 1 which is N-L-aspartyl 2-amino-4-(1-isopropyl-1-cyclopropylmethyl)butanoic acid methyl ester.

* * * * *